US00PP30537P3

(12) United States Plant Patent
Meilland

(10) Patent No.: US PP30,537 P3
(45) Date of Patent: May 28, 2019

(54) FLORIBUNDA ROSE PLANT NAMED 'MEIMACOTA'

(50) Latin Name: *Rosa hybrida*
Varietal Denomination: Meimacota

(71) Applicant: THE CONARD-PYLE COMPANY, West Grove, PA (US)

(72) Inventor: Alain Antoine Meilland, Antibes (FR)

(73) Assignee: The Conard-Pyle Company, West Grove, PA (US)

( * ) Notice: Subject to any disclaimer, the term of this patent is extended or adjusted under 35 U.S.C. 154(b) by 8 days.

(21) Appl. No.: 15/530,625

(22) Filed: Feb. 10, 2017

(65) Prior Publication Data

US 2018/0235121 P1 Aug. 16, 2018

(51) Int. Cl.
*A01H 5/02* (2018.01)
*A01H 6/74* (2018.01)

(52) U.S. Cl.
USPC ..... Plt./150
CPC ..... *A01H 6/749* (2018.05)

(58) Field of Classification Search
USPC ..... Plt./150
See application file for complete search history.

(56) References Cited

PUBLICATIONS

Double Red Knock Out Rose, http://www.soonerplantfarm.com/index.cfm/fuseaction/;home.showpage/pageID.53/index.htm, downloaded Sep. 1, 2018, pp. 1-3.*

* cited by examiner

*Primary Examiner* — Anne Marie Grunberg
(74) *Attorney, Agent, or Firm* — Buchanan Ingersoll & Rooney PC

(57) ABSTRACT

A new and distinct variety of Floribunda rose plant herein referred to by its cultivar name, 'Meimacota', is provided which forms an abundance of attractive, cup-shaped, red colored blossoms on a nearly continuous basis. The vegetation is vigorous and the growth habit is bushy. Attractive, dense, semi-glossy, green foliage is formed. Very good resistance to pests and disease is exhibited, particularly against black spot. Additionally, the new variety is particularly well suited for growing as distinctive ornamentation in the landscape.

1 Drawing Sheet

Botanical/commercial classification: *Rosa hybrida*/Floribunda Rose Plant.

Varietal denomination: cv. Meimacota.

SUMMARY OF THE INVENTION

The new variety of *Rosa hybrida* Floribunda rose plant of the present invention was created during June of 2004 at le Cannet des Maures, Var, France, by artificial pollination wherein two parents were crossed which previously had been studied in the hope that they would contribute the desired characteristics. The female parent (i.e., the seed parent) was the 'Noawel' variety (non-patented in the United States). The male parent (i.e., the pollen parent) of the new variety was the 'Radrazz' variety (U.S. Plant Pat. No. 11,836). The parentage of the new variety can be summarized as follows:

'Noawel' x 'Radrazz'.

The seeds resulting from the above pollination were sown and small plants were obtained which were physically and biologically different from each other. Selective study resulted in the identification of a single plant of the new variety.

It was found that the new Floribunda rose plant of the present invention possesses the following combination of characteristics:

(a) abundantly and substantially continuously forms attractive, cup-shaped, red colored blossoms,
(b) exhibits a bushy growth habit,
(c) forms very dense, semi-glossy, green foliage,
(d) exhibits very good resistance to pests and disease, particularly with respect to black spot, and
(e) is well suited for providing attractive ornamentation.

A new rose variety is provided displaying attractive, cup-shaped red blossoms combined with substantially continuous blossoming and very good disease resistance.

The new variety well meets the needs of the horticultural industry. It can be grown to advantage as ornamentation in parks, gardens, public areas, and in residential landscapes. Accordingly, the plant is particularly well suited for growing in the landscape.

The new variety can be readily distinguished from its ancestors. More specifically, the new variety can be readily distinguished from the seed parental variety, 'Noawel' (non-patented in the United States), in that the new variety exhibits a bushy growth habit, while the seed parent 'Noawel' exhibits a ground cover growth habit. The new variety can be readily distinguished from the pollen parent, 'Radrazz' (U.S. Plant Pat. No. 11,836), in that the new variety displays 48-62 petals on average, while the pollen parent 'Radrazz' displays far fewer petals, only 10 petals on average. Moreover, the new variety can be readily distinguished from related known non-parental varieties. For example, the 'Meipeporia' variety (U.S. Plant Pat. No.

26,298) displays approximately 25 petals, whereas the new variety displays approximately 48-62 petals.

The plant of the new variety was asexually reproduced by rooting of cuttings in le Cannet des Maures, Var, France. The characteristics of the new variety have been found to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Meimacota'.

BRIEF DESCRIPTION OF THE PHOTOGRAPHS

The accompanying photographs show, as nearly true as it is reasonably possible to make the same in a color illustration of this character, typical specimens of the plant parts of the new variety. The rose plant of the new variety illustrated herein was approximately two years of age and was grown outdoors on its own roots at le Cannet des Maures, Var, France, when it was observed in September, 2016. Scale (in centimeters) and comparative standard color information is provided at the bottom of the figure sheet.

Element 1 illustrates a specimen of a young shoot;

Element 2 illustrates a specimen of a floral bud before the opening of the sepals;

Element 3 illustrates a specimen of a floral bud at the opening of the sepals;

Element 4 illustrates a specimen of a floral bud at the opening of the petals;

Element 5 illustrates a specimen of a flower in the course of opening;

Element 6 illustrates a specimen of an open flower—plan view—obverse;

Element 7 illustrates a specimen of an open flower—plan view—reverse;

Element 8 illustrates a specimen of a more fully open flower—plan view—obverse;

Element 9 illustrates a specimen of a more fully open flower—plan view—reverse;

Element 10 illustrates a specimen of a floral receptacle showing the arrangement of the stamens and pistils;

Element 11 illustrates a specimen of a floral receptacle showing the arrangement of the pistils (stamens removed);

Element 12 illustrates a specimen of a flowering stem;

Element 13 illustrates a specimen of a leaf with three leaflets—plan view—upper surface;

Element 14 illustrates a specimen of a leaf with five leaflets—plan view—under surface; and Element 15 illustrates a specimen of a leaf with seven leaflets—plan view—upper surface;

DETAILED BOTANICAL DESCRIPTION

The chart used in the identification of colors is that of The Royal Horticultural Society (R.H.S. Colour Chart—1995 Edition), London, England. The description is based on the observation of two-year-old specimens of the new variety during September while growing outdoors on their own roots at le Cannet des Maures, Var, France.

Class: Floribunda Rose.

*Variety*.—'Meimacota'.

Plant:

*Habit*.—Bushy and intermediate.

*Foliage*.—Very dense with a semi-glossy aspect.

*Height*.—Commonly approximately 70 to 90 cm on average.

Stems:

*Color*.—Commonly near Yellow-Green Group 144A-144B on young stems, and commonly near Yellow-Green Group 146B on old wood.

*Thorns*.—Quantity: commonly approximately 34 small prickles and 19 long prickles on young stems approximately 10 cm in length; commonly approximately 3 long prickles on adult stems approximately 10 cm in length. Size: small prickles are commonly approximately 1-2 mm in length on average; large prickles are commonly approximately 5-7 mm in length on average on young stems and approximately 7-9 mm in length on average on adult stems. Color: commonly near Greyed-Purple Group 183D on young stems, and near Greyed-Orange Group 166A on adult stems. Shape: ovate shaped at the base and slightly curved downward on the upper surface of the thorn and concave on the lower surface of the thorn.

Leaves:

*Leaflets*.—Number: 3, 5, and 7. Length: approximately 5.5 cm on average for a terminal leaflet. Width: approximately 3.2 cm on average for a terminal leaflet. Shape: generally ovate with a cuspidate tip and a rounded base. Margins: serrated and denticulate. Texture: leathery. Color (when young): Upper surface: near Yellow-Green Group 147A. Under surface: near Yellow-Green Group 147B. Color (when fully mature): Upper surface: near Yellow-Green Group 147A. Under surface: near Yellow-Green Group 147B-147C. Anthocyanin coloration: commonly medium anthocyanin coloration on young leaves and shoots and is commonly near Greyed Purple Group 187A.

*Rachis*.—Near Yellow-Green Group 146B in coloration.

*Petioles*.—Commonly approximately 2 cm in length on average, near Yellow-Green Group 146B in coloration, with a slightly glandular upper surface and a few prickles on the under surface.

*Stipules*.—Generally adnate, pectinate, and broad; commonly approximately 1 cm in length and 5 mm in width on average; commonly near Yellow-Green Group 146D in coloration on the upper surface and near Yellow-Green Group 146A in coloration on the under surface.

Inflorescence:

*Number of flowers*.—Commonly 1 to 7 blossoms on average per stem.

*Flowering laterals*.—Mostly no laterals, sometimes 2 to 6 laterals making a corymb inflorescence.

*Peduncle*.—Commonly approximately 5.2 cm in length on average, approximately 4 mm in diameter on average, near Yellow-Green Group 146D in coloration, and commonly exhibiting a glandular surface.

*Sepals*.—Upper surface: generally tomentous in texture and commonly near Yellow-Green Group 148D in coloration. Under surface: generally smooth in texture and commonly near Green Group 143B edged with near Yellow-Green Group 146B in coloration. Size: commonly approximately 1.5 cm in length on average, and approximately 8 mm in width on average. Shape: generally narrow at the top and upright at the base with few extensions measuring approximately 1-1.9 cm in length on average.

*Buds*.—Shape: generally conical. Length: approximately 2.5 cm on average. Diameter: approximately 2 cm on average. Color: when opening, near Red Group 45A slightly suffused with near Red Group 46A on the upper surface and near Red Group 53C on the under surface.

*Receptacle*.—Generally funnel shaped, approximately 6 mm in length and 6 mm in diameter on average, smooth in texture, and near Yellow-Green Group 146C in coloration.

*Flower*.—Shape: cuplike. Diameter: commonly approximately 6-9 cm on average when fully open. Color (when opening begins): Upper surface: near Red Group 53A-53B. Under surface: near Red Group 53C. Color (when fully open): Upper surface: near Red-Purple Group 57C slightly suffused with near Red Group 53C. Under surface: near Red-Purple Group 57D. Fragrance: none. Petal number: commonly approximately 48-62 petals on average under normal growing conditions. Petal arrangement: imbricated without petaloids. Petal length: commonly approximately 3.7 cm on average. Petal width: commonly approximately 2.9 cm on average. Petal shape: cuneiform at the base and rounded at the apex. Petal texture: leathery. Petal drop: good, the petals commonly detach cleanly and freely drop upon full maturity. Petals reflex one-by-one: absent. Stamens: commonly number approximately 53 on average arranged regularly around the styles. Anthers: approximately 2 mm in size on average and commonly near Orange-Red Group 34C edged with near Orange Group 24D in coloration. Filaments: approximately 3 mm in length on average, and the coloration is near Yellow Group 2D. Pistils: commonly number approximately 56 on average. Styles: commonly approximately 1 mm in length on average and near Yellow Group 2D in coloration. Stigmas: commonly approximately 6 mm in diameter on average, and near Yellow-Green Group 44C in coloration. Hips/seed: not observed to date.

Development:

*Vegetation*.—Green, vigorous, and very strong.

*Blossoming*.—Very abundant and substantially continuous, medium in the season.

*Resistance to diseases*.—Very good resistance, particularly with respect to black spot. Plants of the 'Meimacota' variety have not been observed under all possible environmental conditions to date. Accordingly, it is possible that the phenotypic expression may vary somewhat with changes in light intensity and duration, cultural practices, and other environmental conditions.

I claim:

1. A new and distinct rose plant characterized by the following combination of characteristics:

(a) abundantly and substantially continuously forms attractive, cup-shaped, red colored blossoms, (b) exhibits a bushy growth habit, (c) forms very dense, semi-glossy, green foliage, (d) exhibits very good resistance to pests and disease, particularly with respect to black spot, and (e) is well suited for providing attractive ornamentation. substantially as herein shown and described.

* * * * *

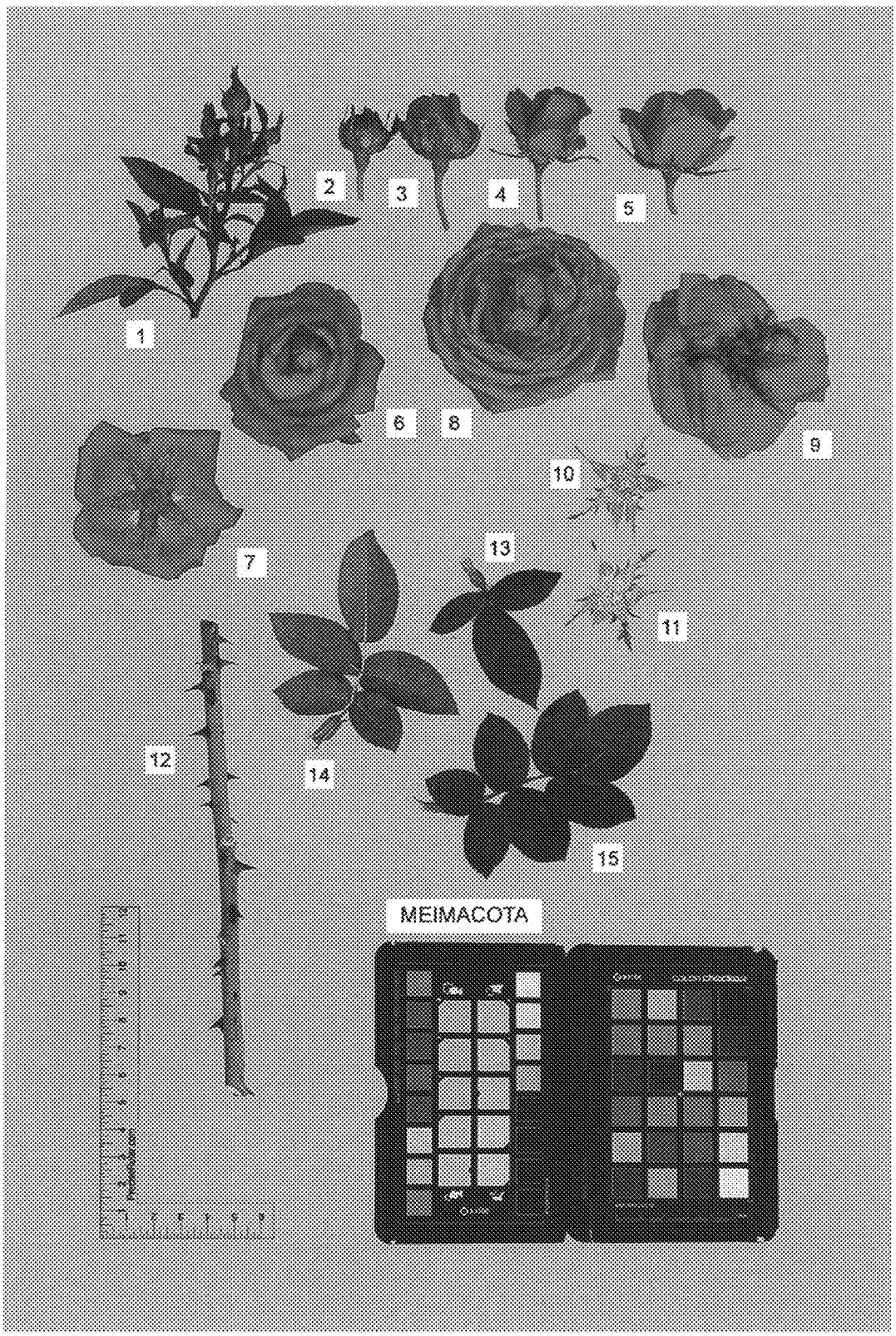
1
2
3
4
5
6
7
8
9
10
11
12
13
14
15
MEIMACOTA